US00PP13078P2

(12) United States Plant Patent
Nelson et al.

(10) Patent No.: US PP13,078 P2
(45) Date of Patent: Oct. 15, 2002

(54) STRAWBERRY PLANT DESIGNATED 'BG-386'

(75) Inventors: Steven D. Nelson; Mike D. Nelson, both of Watsonville; Leo W. Stoeckle, Ventura, all of CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 09/399,950

(22) Filed: Sep. 20, 1999

(51) Int. Cl.[7] ..... A01H 5/00
(52) U.S. Cl. ..... Plt./208

(58) Field of Search ..... Plt./208, 209

*Primary Examiner*—Bruce R. Campell
*Assistant Examiner*—Michelle Kizilkaya
(74) *Attorney, Agent, or Firm*—Foley & Lardner

(57) ABSTRACT

This invention relates to a new and distinct winter planted short-day variety of strawberry known as 'BG-386'. This new variety is primarily adapted to the growing conditions of the southern coast of California. It is particularly characterized by its strong vigorous plant, light colored, moderately sized, uniform conical shaped berries, with fruit and flowers visible above the plant throughout much of the season. The fruit has good flavor, good juiciness and moderately firm texture.

2 Drawing Sheets

SUMMARY OF THE INVENTION

The present invention relates to a new and distinct short-day strawberry variety designated as 'BG-386'. This new variety is a result of a controlled cross of 'PS-592' (U.S. Plant Pat. No. 9,903) and 'Anahiem' (U.S. Plant Pat. No. 8,659). The variety is botanically known as *Fragaria ananassa*.

The seedling resulting from the aforementioned cross was asexually propagated by stolons in a nursery located in Lassen County, Calif., and was subsequently selected from a controlled breeding plot near Oxnard, Calif. in 1996. After its selection, the new variety was further asexually propagated in both Lassen County, Calif. and Siskiyou County, Calif. by stolons and extensively tested over the next several years in fruiting fields near Oxnard, Calif. This propagation has demonstrated that the combination of traits disclosed herein as characterizing the new variety are fixed and remain true to type through successive generations of asexual reproduction.

BRIEF DESCRIPTION OF THE PHOTOGRAPHS

The accompanying color photographs show typical specimens of the new variety at various stages of development as nearly true as it is possible to make in color reproductions:

The first photograph shows a close-up view of typical fruiting field characteristics in mid-April 1999.

The second photograph shows a close-up view of fruit harvested in mid-April 1999 and packed in a standard twelve dry pint crate.

DESCRIPTION OF THE NEW VARIETY

'BG-386' is primarily adapted to the climate and growing conditions of the southern coast of California. This region provides the necessary winter temperatures required for it to produce a strong vigorous plant and to remain in fruit production from January through June. The nearby Pacific Ocean provides the needed humidity and moderate temperatures to maintain fruit quality during the winter and spring production months. The following list of traits in combination define 'BG-386' as a unique variety distinguishing it from the most widely grown commercial variety in the region, 'Camarosa' (U.S. Plant Pat. No. 8,708).

'BG-386' is a large vigorous plant. When provided with optimum chilling in the nursery propagation fields prior to being dug and subsequently artificially cold stored prior to being planted, the plant of the new variety is larger and more vigorous than 'Camarosa'. The plant 'BG-386' is also denser and more upright in growth habit than 'Camarosa'. The foliage of 'BG-386' is slightly darker in color and overall larger in size than the foliage of 'Camarosa' with more serrations per leaf than 'Camarosa'. The leaf blistering of 'BG-386' is medium to strong while the leaf blistering of 'Camarosa' is medium. Petioles of 'BG-386' are longer in length and larger in diameter than the petioles of 'Camarosa'. Table 4 illustrates foliage characteristics of 'BG-386' and 'Camarosa'.

'BG-386' is capable of long season fruit production with fruit of good size and good quality during the entire season when provided with optimum chilling in the nursery propagation fields and artificially cold stored prior to being planted. Fruit production begins in early January, up to 7 days later than 'Camarosa' and may continue cropping into June. 'BG-386' typically produces slightly more runners per plant with a similar season average fruit size and season total fruit yield as 'Camarosa' (Table 1). The crown crop fruit (generally the first fruit to be harvested) of 'BG-386' is typically much smaller as compared to 'Camarosa'. The fruit of 'BG-386' is much smoother with fewer longitudinal creases and better overall appearance and gloss than the fruit of 'Camarosa'. The fruit of 'BG-386' has a lighter skin color than the fruit of 'Camarosa'. The flesh of the fruit of 'BG-386' is moderately firm while the flesh of the fruit of 'Camarosa' is extremely firm. See Table 3 for fruit quality performance ratings. The seeds of 'BG-386' are held even with the surface of the fruit in contrast to 'Camarosa' which tends to have its seeds positioned slightly below the surface. 'BG-386' has a narrow to absent band without achenes under the calyx as compared to 'Camarosa' which has a medium band. The predominant fruit shape of 'BG-386' is conical as compared to 'Camarosa' which tends to be more cylindrical to wedge-shaped. The fruit of 'BG-386' is typically longer than broad while 'Camarosa' is much longer than broad. The calyx of 'BG-386' is generally positioned flat to the berry while the calyx of 'Camarosa' is reflexed. The inflorescence of 'BG-386' is longer and much more visible above the plant canopy than the inflorescence of 'Camarosa' throughout much of the season. See Table 5 for inflorescence characteristics.

For identification, a series of molecular markers have been determined for this new variety.

SPECIFIC DESCRIPTION OF THE NEW VARIETY

The following is a detailed decription of 'BG-386', including the variety's morphological, and pest and disease reaction characteristics. This detailed description is based on observations of fully mature plants taken during the 1999 growing season in Oxnard, Calif. These measurements and ratings were made from plants dug from a high-elevation nursery located in Siskiyou County, Calif. in October 1998 and planted 5 days later in Oxnard, Calif. The yield observations were taken from the 1998–1999 growing season. The characteristics of the new variety may vary in detail, depending upon variations in environmental factors, including weather (temperature, humidity and light intensity), day length, soil type and location without any change in the genotype. 'BG-386' has not been observed under all possible environmental conditions. Color terminology follows the Munsell Book of Colors, Munsell Color, Baltimore, Md. (1976).

Fruit Characteristics

'BG-386' fruit, fruit production and runner production (fruiting field) characteristics as compared to those of 'Camarosa'.

TABLE 1

1998–1999 market fruit yield, fruit size and runner production characteristics from plants harvested from January through June 1, 1998 and 1999 of 'BG-386' dug from a high elevation nursery (Macdoel, California) during the first week of October and planted 4 to 5 days later and compared with 'Camarosa' in Oxnard, California.

| Cultivar | 1998 Total Fresh* Yield GM/PL | 1999 Total Fresh* Yield GM/PL | 1998–1999 Average Fresh* Yield GM/PL | 1998–1999 Average Fruit Size Fresh GRM | 1998 Average Runners/ PL |
|---|---|---|---|---|---|
| 'BG-386' | 686 | 1008 | 847 | 25.6 | 0.7 |
| 'Camarosa' | 661 | 876 | 768 | 24.9 | 3.1 |

*Fresh fruit harvested from January through June 1

TABLE 2

Comparison of primary fruit characteristics of 'BG-386' and '9Camarosa' from Oxnard, California, March 31, 1999.

| Character | 'BG-386' | 1 Camarosa' |
|---|---|---|
| Munsell Color | 7.5 R 4/10 to 7.5 R 3/12 | 5 R 3/8 to 5 R 3/10 |
| Fruit length | | |
| Mean (cm) | 5.2 | 5.7 |
| Range | 4.6–5.8 | 5.3–6.3 |

TABLE 2-continued

Comparison of primary fruit characteristics of 'BG-386' and '9Camarosa' from Oxnard, California, March 31, 1999.

| Character | 'BG-386' | 1 Camarosa' |
|---|---|---|
| Fruit Width | | |
| Mean (cm)* | 5.0 | 4.6 |
| Range | 4.3–6.2 | 3.9–5.1 |
| Fruit Length/Width Ratio | 1.05 | 1.26 |
| Calyx Diameter | | |
| Mean (cm) | 5.9 | 5.7 |
| Range | 4.8–7.2 | 4.5–7.0 |

*Width is measure across the widest part of the berry, typically across the shoulders

TABLE 3

Comparison of 1997–1999 fruit quality characteristics of 'BG-386' and 'Camarosa' from Oxnard, California.*

| Character | 'BG-386' | 'Camarosa' |
|---|---|---|
| Skin Firmness | 7.7 | 8.7 |
| Fruit Appearance | 7.8 | 7.1 |
| Fruit Gloss | 7.9 | 7.5 |

*Results are averaged from 3 years of replicated holding tests performed from January through May 1997–1999. Ratings are based on a scale from 1–10; the higher the rating, the stronger the skin and more attractive and glossy the berry, The fruit is medium-large in size and uniformly conical in shape. Berries are typically longer than wide as described by the length/width ratio. Primary berries are uniformly shaped typically lacking longitudinal creases. The secondary and tertiary berries are also uniformly conical in shape lacking longitudinal creases. The sugar content was taken from a fully mature secondary berry harvested on Feb. 21, 2001 at the Alford Ranch in Oxnard, Calif. The average soluble solid content of the fruit measured in percent Brix is 9.3. The percent Bris is an indirect measurement of the sugar content of the fruit. The fruit surface is light red in coloration with a light red colored flesh. The fruit coloration is even around the surface of the berry. See Table 2 for fruit comparison characteristics. The fruit surface is smooth with the seeds held even with the surface. The second coloration varies from a moderately yellow color to red with prolonged exposure to direct sunlight. The seeds are spaced evenly over the surface of the berry with either a very narrow band or no band without achenes under the calyx. Seedy tipped fruit is very rare. The flesh is moderately firm, moderately glossy and juicy, with good texture and good flavor. See Table 3 for fruit quality characteristics. The calyx is large in size, typically larger than the fruit diameter, with overlapping sepals. The pose of the calyx is almost never reflexed, (typically held flat to the berry). The calyx attaches firmly to the fruit below the surface. Fruit skin is considered only moderately susceptible to cracking due to rain.

Plant Charateristics

Plant height and measurements were made from a fully mature plant on Feb. 21, 2001 at the Alford Ranch in Oxnard, Calif. The plant height ranges from 6–15 cm and averages 10.5 cm. The plant spread ranges from 17–25 cm and averages 20.7 cm. The plant of 'BG-386' is vigorous, large in size with multiple crowns producing a moderate number of runners when given the proper chilling levels prior to being dug, and artificially, prior to being planted. Excessive chilling will result in an over-vigorous, dense plant with a reduction in total fruit yield and increased runner production. The plant is globose in character growing very upright and erect. The plant canopy becomes medium dense to dense when given proper chilling and cold storage.

Foliage Characteristics

'BG-386' foliage characteristics as compared to those of 'Camarosa'.

TABLE 4

Comparison of foliage characteristics of 'BG-386' and 'Camarosa' from Oxnard, California, April 19, 1999.

| Character | 'BG-386' | 'Camarosa' |
|---|---|---|
| Munsell Color (upper surface) | 7.5 GY 3/4 to 7.5 GY 3/6 | 5 GY 3/4 to 5 GY 3/6 |
| Terminal Leaflet Length | | |
| mean (cm) | 8.1 | 7.0 |
| range | 7.2–8.9 | 6.1–8.8 |
| Terminal Leaflet Width | | |
| mean (cm) | 7.3 | 6.6 |
| range | 6.6–8.4 | 6.0–7.7 |
| Terminal Leaflet ratio (L/W) | 1.1 | 1.06 |
| Petiole Length | | |
| mean (cm) | 16.4 | 12.7 |
| range | 14–20 | 7–15 |
| Petiole Width | | |
| mean (mm) | 4.5 | 2.8 |
| range | 4.1–5.2 | 2.1–3.2 |
| Petiolule Length | | |
| mean (mm) | 4.8 | 5.8 |
| range | 3–7 | 5–7 |
| Serrations/Leaf | 22.0 | 17.5 |
| | 18–25 | 15–21 |
| Serration Depth | | |
| mean (mm) | 5.6 | 5.0 |
| range | 4.7–7.1 | 4.6–5.9 |

The Munsell color rating for the lower leaf surface is medium gray green, color varying between 7.5 GY 5/4 and 7.5 GY 6/4 . The foliage of 'BG-386' typically has three leaflets per leaf, is medium to large in size, glossy, medium green in color with medium to strong blistering. The terminal leaflet is longer than wide as described by the length/width ratio, rounded to ovate in shape with an obtuse base. See Table 4 for foliage comparison characteristics. The leaf cross section of an immature terminal leaflet tends to be concave while a fully mature leaflet tends to be slightly concave to flat. Leaflets have many medium sized serrations. These serrations are rounded in shape, typically occur singly, occasionally in doubles. Petioles are considered long and thick in diameter with bract leaflets commonly occurring singly or in pairs on about 50% of the petioles. Pubescence on the petioles is sparse growing irregularly perpendicular to the petiole.

Flowers and Inflorescence

'BG-386' inflorescence and flower characteristics as compared to those of 'Camarosa'.

TABLE 5

Comparison of inflorescence characteristics of 'BG-386' and 'Camarosa' from Oxnard, California, May 29, 1999.

| Character | 'BG-386' | 'Camarosa ' |
|---|---|---|
| Inflorescence Length | | |
| mean (cm) | 34.1 | 28.7 |
| range | 28–37 | 24–33 |
| Primary Peduncle Length | | |
| mean (cm) | 22.6 | 15.2 |
| range | 18–27 | 11–22 |
| Primary Peduncle Width | | |
| mean (mm) | 4.6 | 3.1 |
| range | 4.2–5.5 | 2.7–3.8 |
| Primary Pedicel Length | | |
| mean (cm) | 6.1 | 7.9 |
| range | 4.6–7.6 | 6.5–10.5 |
| Primary Pedicel Width | | |
| mean (mm) | 2.2 | 1.7 |
| range | 1.8–2.7 | 1.3–2.0 |

TABLE 6

Comparison of primary flower characteristics of 'BG-386' and 'Camarosa' from Oxnard, California, April 15. 1999.

| Character | 'BG-386' | 'Camarosa' |
|---|---|---|
| Primary Calyx Diameter | | |
| mean (mm) | 40.5 | 44.9 |
| range | 35–47 | 37–53 |
| Primary Petal Length | | |
| mean (mm) | 15.1 | 12.8 |
| range | 14–16 | 11–14 |
| Primary Petal Width | | |
| mean (mm) | 15.4 | 12.3 |
| range | 13–17 | 11–14 |
| Primary Petal Ratio (L/W) | 0.98 | 1.03 |
| Petals/Primary Flower | 6.7 | 6.4 |
| | 6–8 | 5–7 |
| Primary Sepal Length | | |
| mean (mm) | 17.3 | 18.3 |
| range | 15–21 | 15–22 |
| Primary Sepal Width | | |
| mean (mm) | 8.0 | 8.3 |
| range | 7–9 | 6–10 |
| Primary Sepal Ratio (L/W) | 2.17 | 2.20 |
| Sepals/Primary Flower | 13.0 | 12.7 |
| | 12–16 | 10–15 |

The inflorescence of 'BG-386' is long, extending the flowers and fruit beyond the foliage during much of the season. The peduncle and pedicel counts were made from a fully mature plant on Feb. 21, 2001, from the Alford Ranch in Oxnard, Calif. The number of peduncles ranges from 5–11 and averages 7.9. The number of pedicels per plant ranges from 10–27 and averages 18.3. The primary peduncle is typically non-existent during the early portion of the season then lengthens as the fruiting season progresses. The primary peduncle is considered long in length and thick in diameter late in the season. The pedicel holding the primary berry is considered short and typically originates singly from the apex of the primary peduncle or seldom from one of the secondary peduncles. Secondary and tertiary berries are borne on pedicels arising from secondary peduncle apices. The fruiting truss is typically prostrate at first picking. See Table 5 for inflorescence comparison characteristics. Flowers are medium to large with overlapping petals averaging 6 to 7 large obovate petals per primary flower. The petals are as broad as long as described by the length/width ratio and white in color. The corolla is typically smaller in relative comparison to the calyx. The flower diameter measurements were made from a fully mature primary flower on Feb. 21, 2001 at the Alford Ranch in Oxnard, Calif. The calyx diameter ranges from 44–48 mm and averages 46.1 mm. The corolla diameter ranges from 36–40 mm and averages 37.8 mm. See Table 6 for flower comparison characteristics. The stamen counts were made from a fully mature primary flower on Feb. 21, 2001 and the pistil counts were made from a fully mature secondary flower on Feb. 21, 2001, both at the Alford Ranch in Oxnard, Calif. The number of stamens per flower ranges from 35–43 and averages 39.3. The number of pistils per flower ranges from 227–331 and averages 272. Pollen is produced when the flower becomes fully open and the anthers mature. Typically, a large bract leaf is borne on a petiole which originates at the primary peduncle apex alongside the base of one of the secondary peduncles. Bract leaves occur on nearly every inflorescence. The sepals are elliptical and mostly broad in shape. Weak anthocyanin colorations are present on the stolons, with a munsell color rating between 2.5 YR 5/6 and 2.5 YR 6/6.

Pest Reactions

This new variety may not be resistant to any of the known insects, diseases or viruses common to California. It is known to be moderately susceptible to the two-spotted spider mite, aphid and flower thrips. It is also known to be moderately susceptible to grey fruit mold, powdery mildew and only slightly susceptible to angular leafspot. The susceptibility of the new variety to any of the virus complexes of California has not been determined.

We claim:

1. A new and distinct variety of strawberry plant designated as 'BG-386', as herein described and illustrated by the characteristics set forth above.

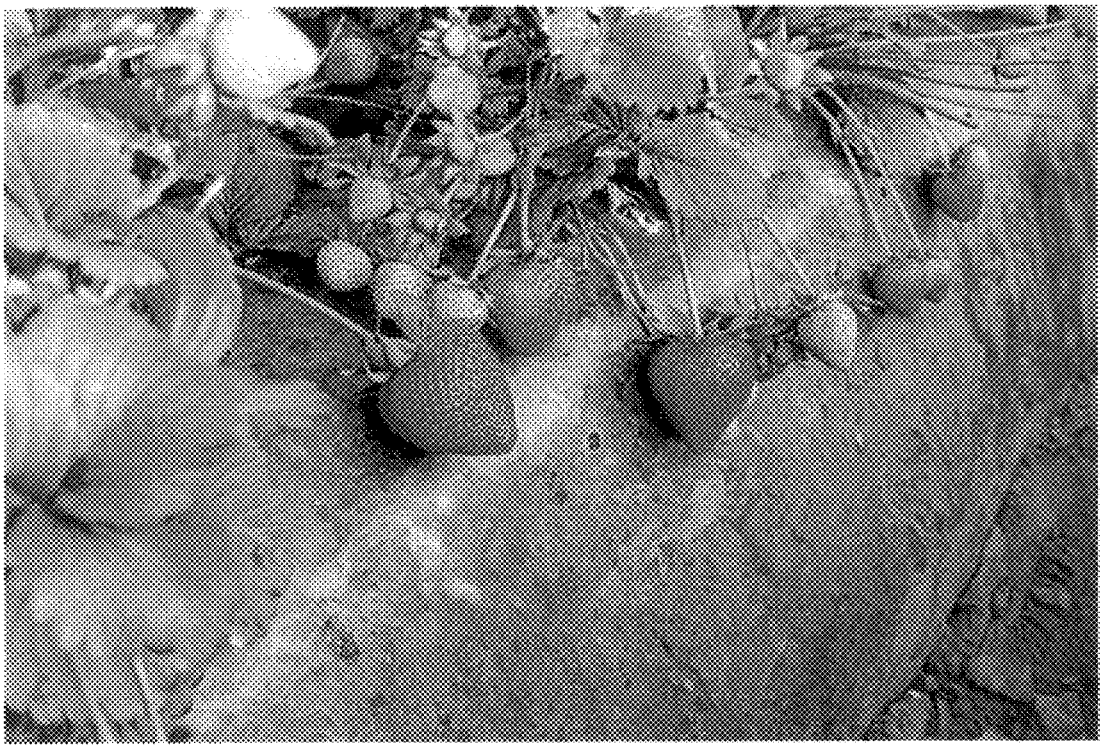

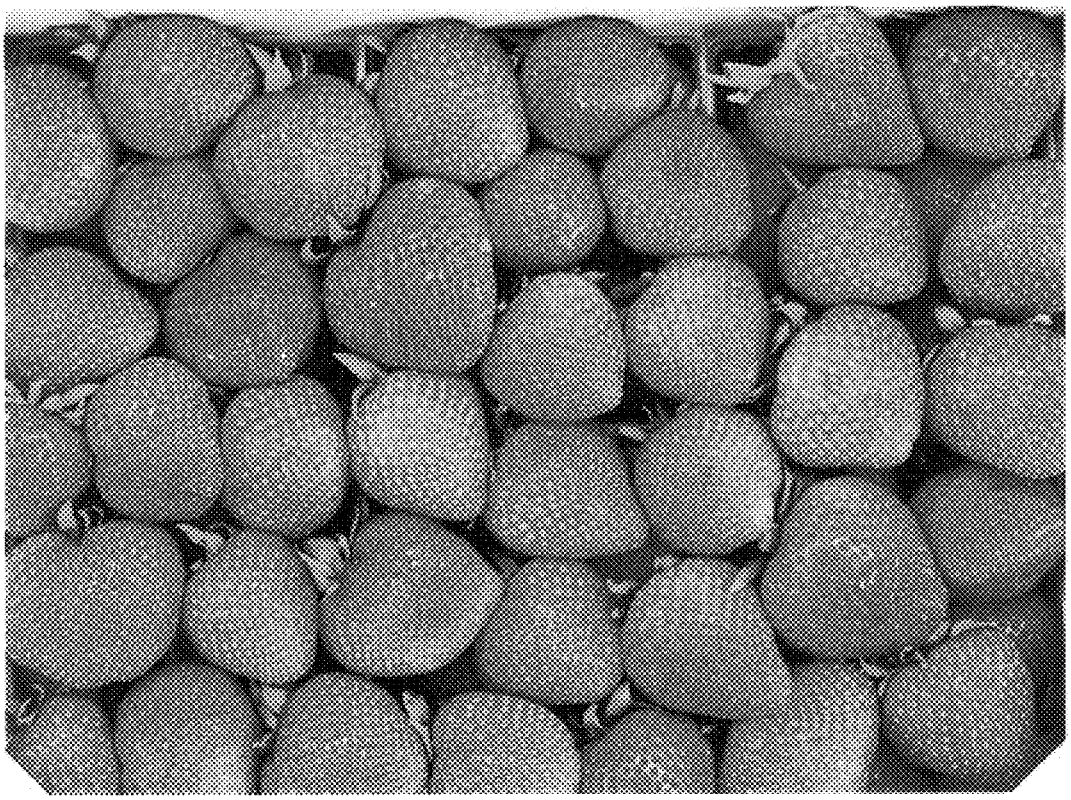

* * * * *